United States Patent
Yoshikawa

Patent Number: 5,043,035
Date of Patent: Aug. 27, 1991

[54] METHOD OF DISASSEMBLING RESIN-MOLDED EQUIPMENT

[75] Inventor: Tetsuji Yoshikawa, Mie, Japan

[73] Assignee: Kabushiki Kaisha Toshiba, Kanagawa, Japan

[21] Appl. No.: 640,517

[22] Filed: Jan. 11, 1991

Related U.S. Application Data

[63] Continuation of Ser. No. 421,649, Oct. 16, 1989, abandoned.

Foreign Application Priority Data

Oct. 25, 1988 [JP] Japan .................. 63-269126
May 11, 1989 [JP] Japan .................. 1-117889

[51] Int. Cl.⁵ .............................. B32B 35/00
[52] U.S. Cl. .......................... 156/155; 156/272.4; 156/273.9; 156/344; 435/872; 219/10.43; 219/10.57
[58] Field of Search ............ 156/155, 272.4, 273.9, 156/344, 584; 219/10.41, 10.43, 10.47, 10.57; 435/872

[56] References Cited

U.S. PATENT DOCUMENTS

| | | | |
|---|---|---|---|
| 2,873,343 | 2/1959 | Collopy | 219/10.47 X |
| 3,292,563 | 1/1975 | Lavins, Jr. | 219/10.57 X |
| 3,662,453 | 5/1972 | Meal et al. | 156/584 X |
| 3,963,417 | 6/1976 | Placek | 156/344 X |
| 4,317,986 | 3/1982 | Sullivan | 156/344 X |
| 4,461,663 | 7/1984 | Tachibang et al. | 156/584 X |

Primary Examiner—Michael W. Ball
Assistant Examiner—Mark A. Osele
Attorney, Agent, or Firm—Philip M. Shaw, Jr.

[57] ABSTRACT

In a method of disassembling resin-molded equipment, a gap is formed in the boundary portion between a metal body and a resin layer disposed around the metal body in order to separate the metal body is separated from the resin layer. To form the gap, either the metal body or the resin layer may be heated, so that the gap is formed by the difference in thermal expansion between the metal body and the resin layer. Alternatively, a microorganism such as ray fungus of Nocardia is attached to the boundary portion between the metal body and the resin layer, and decomposes the resin to form the gap. Since the gap reduces the bonding strength between the metal body and the resin layer and in some cases the metal body may even separate from the resin layer, the metal body may be pulled out with ease.

10 Claims, 3 Drawing Sheets

METHOD OF DISASSEMBLING RESIN-MOLDED EQUIPMENT

This is a continuation of co-pending application Ser. No. 07/421,649 filed on Oct. 16, 1989, now abandoned.

BACKGROUND OF THE INVENTION

The present invention relates to a method of disassembling resin molded equipment such as molded transformers.

Generally, a molded transformer comprises an iron core and a resin-molded coil assembly including an inside cylindrical low-voltage coil and an outside cylindrical high-voltage coil. These coils are together covered with a resin-molded material for insulation.

When such a molded transformer as mentioned above is to be disassembled as the result of expiration of its useful life after use for a certain period, it is particularly difficult to disconnect the resin layer from the coils of the molded coil assembly. In the case of oil-filled transformers, the coil conductors are wound on the iron core with a sheet of oil-immersed insulating paper interposed therebetween and then placed in a metal tank. Subsequently, the tank is filled with an insulating oil. As the result of such construction, the windings may be recycled when the oilfilled transformer is disassembled in the order reverse to that of assembling the same. However, since the resin layer covering the coils is strongly connect to the coils in the molded transformer, the resin layer cannot easily be disconnected from the coils, which makes it impossible to recycle the coils. Furthermore, the used molded coils are liable to be left in dump yards or dumped into the sea, which is not desirable from the standpoint of protection of the beauties of nature or the human environment and which may cause serious social problems.

It has been considered to mechanically crush resin-molded equipment to pieces in order to disassemble the same. Although it is possible to crush the equipment to pieces, not only the resin-molded material but also the metallic parts such as the coil conductors are also broken when the resin-molded equipment is actually crushed to pieces mechanically. Consequently, it is difficult to recycle the metallic parts. Furthermore, there is the possibility that the crushing may produce noise and minute particles of resin, metal or other materials wafting in the atmosphere, which is not desirable from the standpoint of public health.

SUMMARY OF THE INVENTION

Therefore, an object of the present invention is to provide a method of disassembling resin-molded equipment wherein a resin-molded metallic body can be separated from a resin layer with ease without a large external force applied to the metallic body.

The present invention provides a method of disassembling resin-molded equipment comprising the steps of forming a gap in a boundary portion between a metallic body and a resin layer provided around the metallic body so as to enclose the same and separating the metallic body from the resin layer by making use of the gap.

According to the above-described method, the degree of bonding between the metallic body and the resin layer is lowered by forming the gap in the boundary portion between the metallic body and the resin layer. In this state, the metallic body is separated from the resin layer. Consequently, the external force necessary for the separation is small, thereby rendering the disassembling work easy.

It is preferable that the gap be formed in the boundary portion between the metallic body and the resin layer by causing a microorganism to act on the boundary portion. Furthermore, it is preferable that the microorganism include Nocardia in the order of ray fungi.

The gap may also be formed by means of difference of thermal expansion between the metallic body and the resin layer as the result of heating at least one of the metallic body and the resin layer by a heating means.

The heating means may be an electromagnetic induction heating apparatus establishing a high frequency magnetic field generating an induction current in the metallic body.

The heating means may also be a power supply which supplies the metallic body with an electric current so that the Joule's heat is generated in the metallic body.

Furthermore, the heating means may be an electrode disposed on the outer periphery of the resin layer and a high frequency power supply provided for applying a high frequency voltage across the electrode and the metallic body.

Other objects of the present invention will become obvious upon an understanding of the illustrative embodiments about to be described or will be indicated in the appended claims. Various advantages not referred to herein will occur to one skilled in the art upon employment of the invention in practice.

BRIEF DESCRIPTION OF THE DRAWINGS

In the accompanying drawings

DESCRIPTION OF THE PREFERRED EMBODIMENT

A first embodiment wherein a transformer comprising a resin-molded coil assembly is to be disassembled will now be described with reference to FIGS. 1 to 3 of the accompanying drawings. A microorganism and more specifically, Nocardia in the order of ray fungi is employed for forming a gap in the method of the first embodiment, as will be described in detail later. The ray fungus releases oxygen such that the carbonic double bond of epoxy resin molecules is severed and the oxygen is linked to the carbon atoms. FIG. 3 illustrates the relationship between the temperature of a sample piece and the decomposition rate decomposition rate of the sample piece caused by a ray fungus. As shown in FIG. 3, the decomposition rate of the ray fungus is relatively high at an ambient temperature of approximately 35° C., i.e. or the ray fungus is relatively active at the ambient temperature of approximately 35° C. When the net weight of the material decomposed at 35° C. is considered as 100%, the ray fungus has characteristics such that the decomposition rate thereof is decreased to 90% at 20° C. and to 77% at 10° C. When the ambient temperature is further decreased, the ray fungus becomes still less active. The ray fungus also becomes less active when the ambient temperature is increased to 50° C. or above. The ray fungus is killed when the ambient temperature is increased to 60° C. or above.

Figure 1:
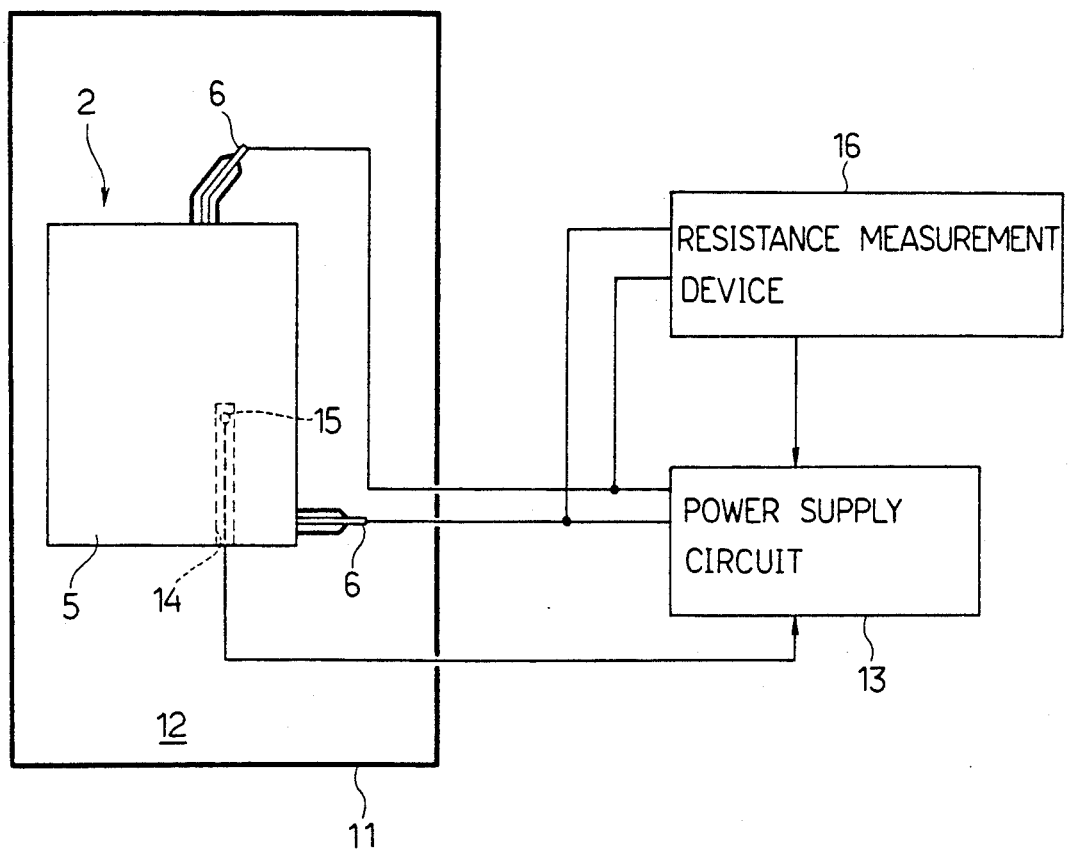
FIG. 1 is a schematic illustration of facilities for executing the method of one embodiment of the invention.
Figure 2:
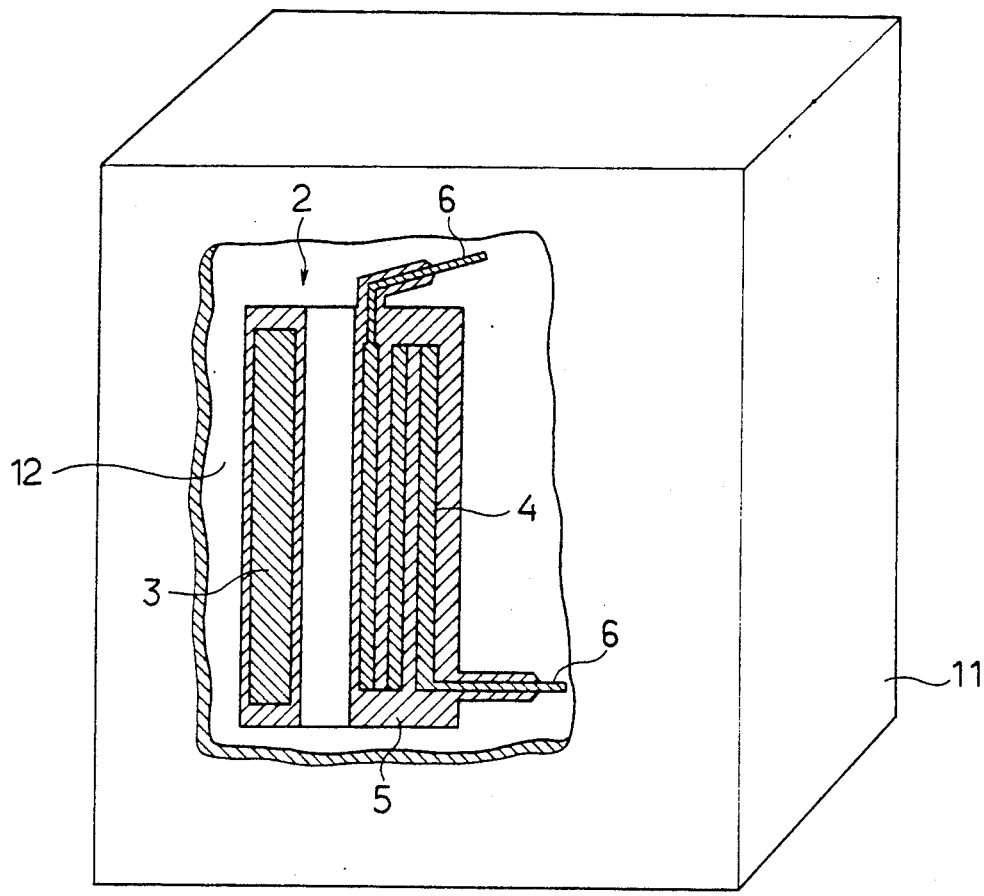
FIG. 2 is a schematic perspective view, partially broken, of the major part of the facilities in FIG. 1.
Figure 3:
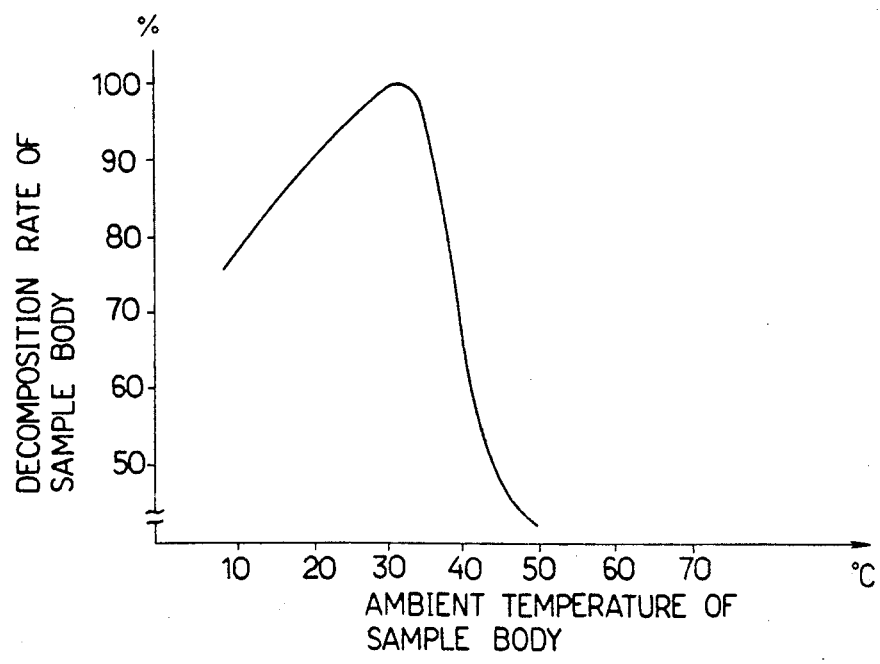
FIG. 3 is a graph showing the relationship between the temperature of a sample piece and the decomposition rate of the sample piece caused by a ray fungus.

Referring to FIGS. 1 and 2, reference numeral 11 designates a housing defining a processing compartment 12 filled with air or oxygen. The processing compartment 12 may be formed by partitioning a working space of a building. The building may be furnished with air conditioning system so that the indoor air is cooled. Alternatively, an industrial or household refrigerator may be employed for providing the processing compartment 12. The ambient temperature of a resin-molded coil assembly 2 or other resin-molded equipment is set to a temperature between 0° and 10° C. The resin-molded coil assembly 2 comprises a cylindrical low-voltage coil 3, a cylindrical high-voltage coil 4 disposed outside the low-voltage coil 3, and a resin layer 5 molded from resin for enclosing the coils 3 and 4 together. A power supply circuit 13 with an output adjusting function is connected to terminals 6 of the coil 4 of the resin-molded coil assembly 2. The resin layer 5 of the molded coil assembly 2 has a hole formed in the portion thereof in the vicinity of the coil 4 by means of drilling. A temperature sensor 15 is inserted in the hole 14. A resistance measurement device 16 is connected to the terminals 6 of the winding 4. The power supply circuit 13 is adapted to feed an electric current to the coil 4 so that the coil 4 generates heat. The output of the power supply circuit 13 or the output voltage thereof is controlled so that the temperature of a boundary portion between the resin layer 5 and coil 4 reaches approximately 35° C. More specifically, the power supply circuit 13 is adapted to control the output voltage based on a temperature signal obtained based on the resistance value measured by the resistance measurement device 16, whereby the temperature of the coil 4 heating is controlled to be approximately 35° C. A temperature sensor 15 is provided for sensing the temperature of the resin layer 5, thereby producing a control signal. The control signal is supplied to the power supply circuit 13 or the air conditioner which controls the temperature of the resin layer so that the temperature of the resin layer is usually maintained at temperature lower than that of the coil 4. Such control of the temperature of the resin layer 5 is made in order that the ray fungi act concentrically on the boundary portion between the coil 4 and the resin layer 5.

The ray fungi are attached to the terminals 6 of the coil 4 and the temperature of the boundary portion between the resin layer 5 and the coil 4 is maintained at approximately 35° C. Since the ambient temperature of the molded coil assembly 2 ranges between 0° and 10° C. and the temperature of the boundary portion is maintained at approximately 35° C., the ray fungi gather to the boundary portion and become active there. The ray fungi go inward with the boundary portion oxidized to be decomposed. It takes about two months to decompose 3 to 4% of the molded coil assembly 2 from the outer surface thereof when the entire coil assembly 2 is maintained at the temperature of approximately 35° C. However, when the temperature of the portion of the coil assembly 2 in the vicinity of the coil 4 is concentrically controlled to be approximately 35° C., the portion of the coil assembly 2 in the vicinity of the coil 4 may be concentrically decomposed by the ray fungi, whereby the bond between the coil 4 and the resin layer 5 may be rapidly released. Consequently, a gap is formed in the boundary portion of the coil 4 and the resin layer 5. The gap may or may not completely separate the coil 4 from the resin layer 5. Even when the gap thus formed does not cover all of the boundary portion between the coil 4 and the resin layer 5, the coil 4 may be separated from the by resin layer 5 with ease by the application of a relatively small external drawing or pushing force to the coil 4 since the gap formed serves to reduce the bonding strength between the coil 4 and the resin layer 5. Thereafter, the coil 4 is pulled out and recycled.

The resin layer 5 may or may not be broken into pieces so as to be employed for reclamation or as building materials. Alternatively, the resin layer 5 may be continuously decomposed by the ray fungi even after the separation from the coil 4 with the temperature thereof maintained at approximately 35° C. The resin layer 5 is finally decomposed to carbon dioxide and water, which may be collected to be recycled for plant cultivation at farms or the like. Since the ray fungi become less active in the temperature range between $-10°$ and 0° C, the ray fungi may be preserved in a glass vessel or the like in that temperature range. Additionally, the low-voltage coil 3 may be separated from the resin layer 5 in the same manner as described above According to the foregoing embodiment, the gap is formed in the boundary portion between each of the coils 3, 4 and the resin layer 5 and thereafter the coils 3, 4 are separated from the resin layer 5. Thus, the coils 3, 4 may be separated from the resin layer 5 with ease and collected so as to be recycled. Furthermore, organic substances of the resin layer 5 may be decomposed without resin dust produced during the disassembling.

Although the ray fungus is employed as the microorganism in the foregoing embodiment, other microorganisms acting in the same manner as described above may be employed. Although both of the temperature sensor 15 and the resistance measurement device 16 are employed for controlling the temperature of the boundary portion between the coils and the resin layer, either one of them may be employed for sensing the temperature of the portion of the coil assembly in the vicinity of the coils. Furthermore, when the outdoor temperature is below 10° C., the processing compartment 12 may or may not be provided. Additionally, in the case where the molded transformer is split owing to an accident during operation with the windings cut off and cut winding ends are exposed from the split portion, the transformer may be separated from the resin layer in the above-described manner when an electric current can be caused to flow into the cut winding ends from the outside.

Figure 4:
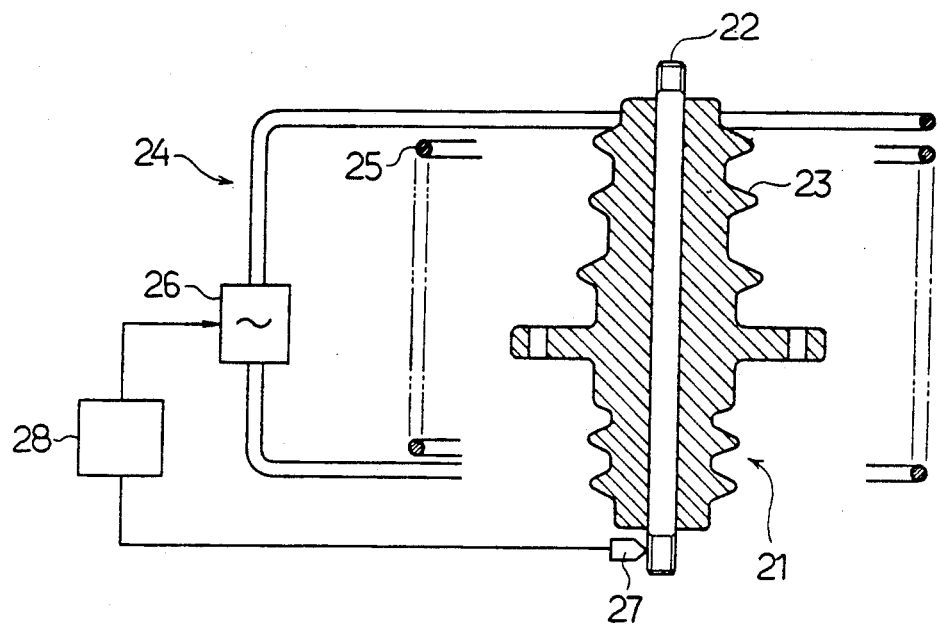
FIG. 4 is a schematic illustration of facilities for executing the method of a second embodiment of the invention.

A second embodiment of the invention will now be described with reference to FIG. 4. In this embodiment, a resin-molded bushing 21 is adopted as the resin-molded equipment. The resin-molded bushing 21 is disassembled by making use of a difference in thermal expansion, as will be hereinafter described in detail. The resin-molded bushing 21 has a round bar like central conductor 22 covered with resin-molded material. Reference numeral 23 designates the resin layer. An electromagnetic induction heating apparatus 24 is provided around the resin-molded bushing 21 for heating the central conductor 22. As is well known in the art, the electromagnetic induction heating apparatus 24 comprises an induction coil 25 and a high frequency power supply 26 supplying a high frequency current to the induction coil 25. An electromagnetic field provided by the induction coil 25 causes an induction current in the central conductor 22. The Joule's heat generated by the induction current causes the central conductor 22 to self-heat. The temperature of the central conductor 22 is sensed by a temperature sensor 27. Based on the sensed temperature, control means 28 controls the amount of high frequency current supplied to the central conductor 22 from the high frequency power supply 26.

When the central conductor 22 is heated, the difference of thermal expansion between the central conductor 22 as a metallic body and the resin layer 23 causes a tearing force between them. For example, the thermal expansion coefficient of copper is $20 \times 10^{-6}/°$ C. and that of epoxy resin is $180 \times 10^{-6}/°$ C. Thus, a gap is gradually formed in the boundary portion between the central conductor 22 and the resin layer 23. After a sufficient gap is formed, the central conductor 22 is separated from the resin layer 23 and pulled out to be recycled. The resin layer 23 may or may not be broken into pieces so as to be employed for reclamation or as building materials.

The same effect as in the first embodiment is achieved in the second embodiment. In particular, the disassembling work may be performed in a relatively short period in accordance with the method of the second embodiment.

Although the central conductor 22 is induction heated by the induction heating apparatus 21 in the second embodiment, a low frequency current or DC current may be directly supplied to the central conductor 22 so that the conductor 22 is caused to self-heat.

Figure 5:
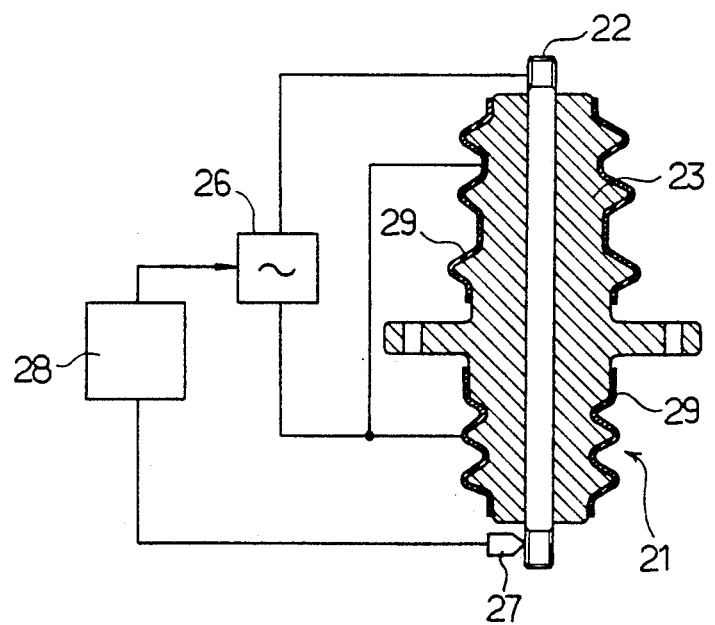
FIG. 5 is a view similar to FIG. 4 showing a third embodiment of the invention.

FIG. 5 shows a third embodiment. In the case of disassembling the resin-molded bushing 21 by making use of the difference of thermal expansion, the resin layer may be heated by a dielectric heating of apparatus instead of the metallic body, as shown in FIG. 5. An electrode 29 having less than one turn is provided around the resin layer 23 of the bushing 21. A high frequency voltage from the high frequency power supply 26 is applied across the electrode 29 and the central conductor 22. Consequently, heat resulting from dielectric loss is applied to the resin layer 23. The difference of thermal expansion between the central conductor 22 and the resin layer 23 causes a gap in the boundary portion therebetween. The same effect as in the first embodiment may thus be achieved in the third embodiment.

The foregoing disclosure and drawings are merely illustrative of the principles of the present invention and are not to be interpreted in a limiting sense. The only limitation is to be determined from the scope of the appended claims.

What I claim is:

1. A method of disassembling resin-molded equipment having a metallic body surrounded by a resin layer, comprising the steps of:
   a) causing a microorganism to act on a boundary portion between the metallic body and the resin layer so that a gap is formed in the boundary portion between the metallic body and the resin layer; and
   b) separating the metallic body from the resin layer by making use of the gap.

2. A method of disassembling resin-molded equipment according to claim 1, wherein the microorganism includes Nocardia in the order of ray fungi.

3. A method of disassembling resin-molded equipment according to claim 1, wherein the microorganism is caused to act on the boundary portion while heat is concentrically applied to the boundary portion.

4. A method of disassembling resin-molded equipment according to claim 3, wherein the microorganism is caused to act on the boundary portion while the ambient temperature of the resin layer is maintained at a temperature lower than that of the boundary portion.

5. A method of disassembling resin-molded equipment according to claim 3, wherein a portion of the metallic body is exposed from the resin layer and the microorganism is attached to the equipment in the vicinity of the exposed metallic portion such that formation of the gap is initiated at the exposed portion.

6. A method of disassembling resin-molded equipment having a metallic body surrounded by a resin layer comprising causing a microorganism to act on the resin layer so that the resin layer is decomposed, thereby allowing the metallic body to be removed.

7. A method of disassembling resin-molded equipment according to claim 6, wherein the microorganism includes Nocardia in the order of ray fungi.

8. A method of disassembling resin-molded equipment having a metallic body substantially encased in a resin layer, comprising the steps of:
   a) a heating the metallic body by use of an electromagnetic induction heating apparatus which establishes a high frequency magnetic field around the metallic body so that an induction current is generated in the metallic body, such that a gap is formed between the metallic body and the resin layer by means of their different thermal expansion; and
   b) separating the metallic body from the resin layer by making use of the gap.

9. A method of disassembling resin-molded equipment having a metallic body substantially encased in a resin layer, comprising the steps of:
   a) heating the metallic body by supplying the metallic body with a sufficiently large electric current that Joule heat is generated in the metallic body, thereby forming a gap between the metallic body and the resin layer by means of their different thermal expansion; and
   b) separating the metallic body from the resin layer by making use of the gap.

10. A method of disassembling resin-molded equipment having a metallic body surrounded by a resin layer, comprising the steps of:
   a) heating the resin layer by use of a dielectric heating apparatus which includes an electrode disposed on the outer periphery of the resin layer and a high frequency power supply which applies a high frequency voltage across the electrode and the metallic body, resulting in a dielectric loss which heats the resin layer, such that a gap is formed between the metallic body and the resin layer by means of their different thermal expansion; and
   b) separating the metallic body from the resin layer by making use of the gap.

* * * * *